United States Patent [19]
Johnson et al.

[11] Patent Number: 5,879,309
[45] Date of Patent: Mar. 9, 1999

[54] PERSONAL MOTION EVENT MONITOR

[76] Inventors: Mark A. Johnson, 55 Brinker Dr. South, Rensselaer, N.Y. 12144; Paul J. Cote, 32 Reed La., Clifton Park, N.Y. 12065

[21] Appl. No.: 919,182

[22] Filed: Aug. 11, 1997

Related U.S. Application Data

[63] Continuation of Ser. No. 805,199, Feb. 27, 1997, abandoned, which is a continuation of Ser. No. 596,396, Feb. 12, 1996, Pat. No. 5,610,890, which is a continuation-in-part of Ser. No. 443,911, May 18, 1995, Pat. No. 5,523,742, which is a continuation-in-part of Ser. No. 312,853, Sep. 23, 1994, abandoned, which is a continuation of Ser. No. 154,324, Nov. 18, 1993, abandoned.

[60] Provisional application Nos. 60/000,970 Jul. 7, 1995 and 60/038,900 Feb. 27, 1997.

[51] Int. Cl.[6] ............................................. A01B 5/00
[52] U.S. Cl. ............................................ 600/552; 600/595
[58] Field of Search .................... 600/510, 552, 600/553, 587

[56] References Cited

U.S. PATENT DOCUMENTS

| | | | |
|---|---|---|---|
| 5,008,654 | 4/1991 | Callaway | 340/686 |
| 5,146,206 | 9/1992 | Callaway | 340/573 |
| 5,247,939 | 9/1993 | Sioquist et al. | 600/570 |

*Primary Examiner*—Carey E. O'Connor
*Assistant Examiner*—Pamela L. Wingood
*Attorney, Agent, or Firm*—John F. Moran; Michael C. Sachs

[57] ABSTRACT

A motion detection device for monitoring patient movement. The device includes a sensor adapted to generate a voltage from mechanical vibrations and a circuit in operable relationship with the voltage for generating an alarm upon detection of a predetermined signal. The circuit provides a fixed impedance to the sensor. A micro controller is used for analyzing the signal to select from first and second conditions by sensing activity within sequences of preselected time intervals. The first condition represents a medical condition and the second condition represents casual motion. A switch is used for setting a time interval and a total sampling time for the micro controller. An alarm signal generates an alarm upon detection by the microprocessor of a predetermined activity. The preferred sensor comprises a housing having an outer shell and a hollow spherical opening therein. A plurality of inner spherical bodies are adapted to move freely inside the spherical opening to produce detectable mechanical vibration in the outer shell. A piezoelectric film is attached to a portion of the outer shell to generate a voltage from the mechanical vibrations.

7 Claims, 2 Drawing Sheets

PERSONAL MOTION EVENT MONITOR

This application claims benefit of the filing date of provisional application Ser. No. 60/038,900 filed Feb. 27, 1997 and also is a continuation of application 08/805,199 filed Feb. 27, 1997, now abandoned, which itself is a continuation of 08/596,396 filed Feb. 12, 1996 now U.S. Pat. No. 5,610,590, which in turn is a CIP of (both 60/000,970 filed Jul. 7, 1995 and also of) 08/443,911 filed May 18, 1995 now U.S. Pat. No. 5,523,742, which itself is a CIP of 08/312,853 now abandoned filed Sep. 23, 1994, which in turn is a continuation of 08/154,324 now abandoned filed Nov. 18, 1993, the entire file wrapper contents of which applications are herewith incorporated by reference as though fully set forth herein at length.

FIELD OF THE INVENTION

The present invention relates to a monitoring device for individuals who are afflicted with disorders such an epilepsy that manifest themselves as anomalous physical activity. More particularly the present invention relates to a motion sensor which more effectively rejects false alarms and yet is able to detect a particular type of motion over a preselected period of time to then trigger an alarm upon recognition of that type of motion.

BACKGROUND OF THE INVENTION

Epilepsy is a disorder of the brain characterized by recurring seizures, in which there are uncontrolled electrical discharges of brain cells. Epilepsy may arise from a very small area of damaged brain tissue, or from the entire brain. There may be no apparent brain damage, or damage may be limited to an area so small it cannot be detected. Therefore, in nearly one-half the cases, the cause of epilepsy is unknown.

There are several types of seizures associated with epilepsy, the most common of which are generalized tonic-clonic (grand mal), absence (petit mal), complex partial (psychomotor), and elementary partial (focal motor). Each seizure type can be characterized by various symptoms. However, the seizures are generally not life threatening, lasting at most up to three minutes. The exception is status epilepticus, also called continuous seizure state. This is the occurrence of repetitive or continuous seizures and affects approximately 3 to 5% of those individuals suffering from epilepsy. It can exist with all types of seizures and may result in irreversible brain damage or death without prompt medical treatment.

Prior to the invention described in U.S. Pat. No. 5,523, 742, parents of children afflicted with epilepsy, particularly status epilepticus, did not have a device for alerting the parents when the child may be having an epileptic seizure during sleeping hours. One recourse had been for the parents to sleep with the child, in the same bed, hoping to be awakened by the seizure during its early stages when the seizure motion may be quite mild. Often, the parents would choose to supplement this safeguard by using an alarm clock, set to sound every hour, to awaken and observe the state of the child. This, of course, places an extraordinary burden on both the child and the parents and is inherently unreliable as seizures may occur at any time. Moreover, the intermittent sleep afforded the parents as well as the desire for privacy by the child and by the parents make the procedure impractical and inefficient.

Continuous visual monitoring of the afflicted individual is usually impossible and periodic monitoring is often insufficient.

Monitors described in U.S. Pat. Nos. 5,523,742 and 5,610,590 provide relief during sleeping hours, but are inappropriate for reliably discriminating anomalous activity from the casual motion associated with normal quiet daytime activities. The use of either of these monitors would produce an unacceptably high false alarm rate resulting in undue anxiety and a loss of faith in the device.

One motion sensor that has found some applicability is disclosed in European Patent No. 87110092.1, filed Jul. 13, 1987. This device detects motion using a single moving object rolling on solid surfaces in which either the object or the surface, or both, have facets that interrupt the movement of the object on the surface. That sensor, of course, is intended to control the functioning of, heart pacemakers, which presents entirely different technical and medical problems to solve. For this reason, the European Patent is able to use microphones to sense the activity of the object, thus consuming considerable electric power.

Motion sensor devices are obvious solutions to the aforementioned problem, provided that such devices be designed to ignore the casual motions of a child (rolling over, etc.) while responding to those motions characteristic of a seizure, however mild at the beginning. Existing motion sensor devices such as accelerometers or displacement followers could conceivably be designed to detect certain types of motion while ignoring others, but are invariably expensive, consume excessive power, and, when the required signal conditioning equipment is included, form a bulky package. Moreover, these devices commonly require electrical connections between the transducer (affixed to the patient) and its associated equipment located near, but not on, the patient.

Accordingly, it is an object of this invention to provide a device for sensing a type of motion of concern while ignoring, for the most part, other non-harmful motion such as ordinary movement.

Another object of this invention is to provide a monitoring device for use during the day time as well as at night.

Still another object of this invention is to provide a monitoring device in which the user is able to attend class or do other activities without setting off unacceptably frequent false alarms.

Yet another object of this invention is to provide a simple, effective device for monitoring epileptics using a sensor that is easy to manufacture.

Other objects will appear hereinafter.

SUMMARY OF THE INVENTION

It has now been discovered that the above and other objects of the present invention may be accomplished in the following manner. Specifically, the invention comprises a motion detection device for use as a monitor for anomalous patient movement, along with an improved sensor for use with the monitors of this invention and also with other monitoring systems.

The present invention provides an improved monitor for detecting patient movement, particularly in sedentary activities such as attendance in a classroom. The motion detection device of the present invention is designed to including monitoring daytime patient movement. It includes a sensor adapted to generate a voltage from mechanical vibrations and circuit means in operable relationship with the voltage for generating an alarm upon detection of a predetermined signal.

The circuit including impedance means presenting a fixed impedance to the sensor to modify the signal for use with a micro controller. The micro controller analyzes the signal to select from first and second conditions by sensing activity within sequences of preselected time intervals. The first condition represents a medical condition and the second condition represents casual motion. A switch is provided for setting a predetermined time interval and a total sampling time for the micro controller. An alarm for receiving an alarm signal from the microprocessor is included, which signal is generated upon detection by the microprocessor of a predetermined medical condition activity.

The motion detection device further includes low battery detection means for detecting a low battery condition and sounding an alarm indicative thereof. The sensor is suitable to be attached to a patient for generating motion signals in response to movement of the patient.

The preferred motion detection device further includes a reset switch for resetting the device to an operable condition after activation of the alarm. For daytime use, the microprocessor includes a micro code substantially as set forth in Table I hereinafter. However, The motion detection device may further include nighttime detection means including a switch to selectively activate a radio transmitter incorporated in the circuit to transmit the alarm signal to a remote compatible receiver for receiving the transmitted signal to activate an alarm means at the remote location.

The preferred sensor is formed from a housing having an outer shell and a hollow spherical opening therein. A plurality of inner spherical bodies are position inside to move freely inside the spherical opening to thereby produce detectable mechanical vibration in the outer shell when the sensor is moved, whether by casual movement or a medical condition. A piezoelectric film is attached to a portion of the outer shell so that the film generates a voltage from the mechanical vibrations.

In the preferred sensor, the outer shell comprises a pair of cylinders having a hemispherical volume removed therefrom to form the spherical opening. One of the cylinders includes a flat surface for attachment of the piezoelectric film.

BRIEF DESCRIPTION OF THE DRAWINGS

For a more complete understanding of the invention, reference is hereby made to the drawings, in which.

DETAILED DESCRIPTION OF THE PREFERRED EMBODIMENT

The sensor of the present invention is simple and has been designed to be a robust means for detecting anomalous physical activity in an individual, such as where the anomalous activity may, for example, be that associated with a seizure episode. Upon activation by physical motion, whether from a seizure or from casual, non threatening motion, the sensor generates a voltage output that provides a measure of the amplitude and the frequency of the motion. It is isotropic, that is, the output is essentially insensitive to the direction of motion or the orientation of the user. The monitor is not intended for use during vigorous activities, such as play at recess and the like. It is small, lightweight, portable, simple to use, and inexpensive to produce.

Figure 1:
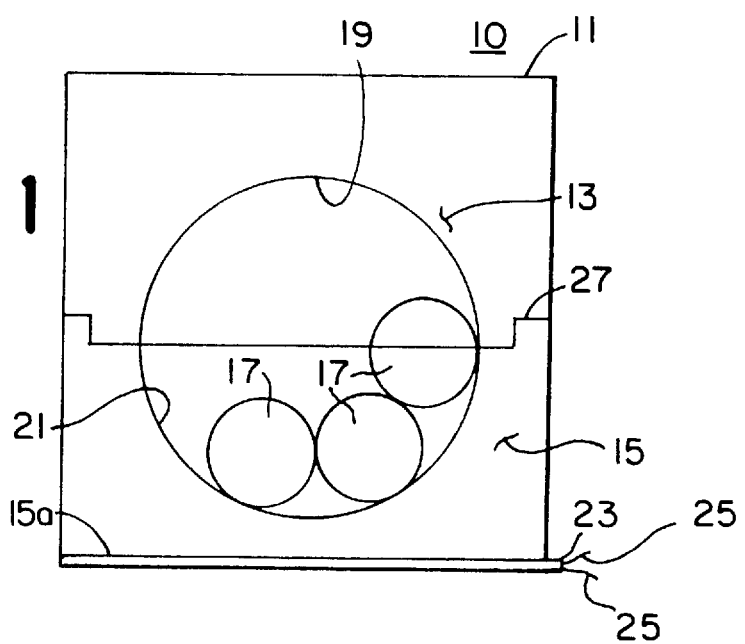
FIG. 1 is a schematic, side elevational view in section of the sensor of this invention.

As shown in FIG. 1, a sensor 10 generally includes a housing 11 formed from an upper half 13 and a lower half 15. The operating principle of the sensor is based on detection of mechanical vibrations generated by the motion and impacts of the multiple spheres within a spherical outer shell. The preferred embodiment uses a piezoelectric film attached to the outer shell to detect the vibrations set up within the outer shell by the moving spheres 17. Both upper half 13 and lower half 15 (with the terms upper and lower being relative to the orientation of the device) have hemispherical volumes 19 and 21 respectively so that spheres 17 are free to move within the spherical opening or volume defined by those hemispherical volumes 19 and 21.

As part of the sensor, a piezoelectric film 23 is attached to outer shell 11 to detect the vibrations set up within the shell by the moving spheres 17. The relative sizes of the inner spheres 17 and outer shell 11 (and the hemispherical volumes 19 and 21) are selected to allow adequate amplitude of internal motion of the plurality of spheres 17 to produce detectable mechanical vibration in the outer spherical shell 15, in this case, which are transmitted to the piezoelectric film 23 to generate a voltage carried by wires 25.

The multiple spheres 17 serve two main purposes. First, the plurality of spheres 17 promote a more isotropic response to motion through the randomization of the impacts on the inner surfaces 19 and 21 of the outer shell portions 13 and 15. Experiments with a single inner sphere shows measurable orientation effects from differences in piezoelectric film output depending upon whether the single sphere impacts on inner surface 19 which is remote from film 23 or surface 21 which is proximate film 23. A single sphere arrangement may be adequate for applications where orientation effects are not a concern.

The second purpose of the use of a plurality—preferably at least two—of spheres 17 is to enhance discrimination between large amplitude, continuous, repetitive activity associated with anomalous activity and the casual, gentle motions associated with normal, quiet, home activities or with normal classroom activities. Experiments with multiple spheres 17 show that they tend to arrange in a stable equilibrium configuration within the outer shell 11 that tends to resist motion for small, subtle disturbances. This stable configuration is attributed to the static frictional forces at the multiple points of contact between the spheres 17 and the shell walls 19 and 21. The advantage offered by this embodiment is that small, subtle motions tend to leave the plurality of spheres 17 locked in their static configuration. On the other hand, the large, energetic motions associated with certain medical disorders are sufficient to promote movement of the spheres 17 with random, energetic impact on shell walls 19 and/or 21.

In one preferred embodiment, the multiple inner spheres 17 are two solid brass balls with a diameter of 0.094 inches. The spherical volume in the present implementation is fabricated by joining two steel cylinders 13 and 15, each of which have a milled out hemispherical volume 19 and 21 respectively of 0.25 inch diameter. A mating circular lip 27 is also provided to serve as an alignment guide for halves 13 and 15 to form shell 11. The joining of the outer shell halves 13 and 15 is made permanent by a spot welding process.

The piezoelectric film 23 is available from commercial vendors and is cut to fit the outer surface of the outer shell construction as shown in FIG. 1. In this embodiment, film 23 is attached to one of the flat surfaces 15a of lower shell cylinder 15. The voltage generated within film 23 from the vibrations caused by the impacting spheres 17 is fed from the two film electrodes 25 into the electronic circuit shown in FIG. 2 that analyzes the signal and triggers an alarm if certain preset conditions are met.

Figure 2:
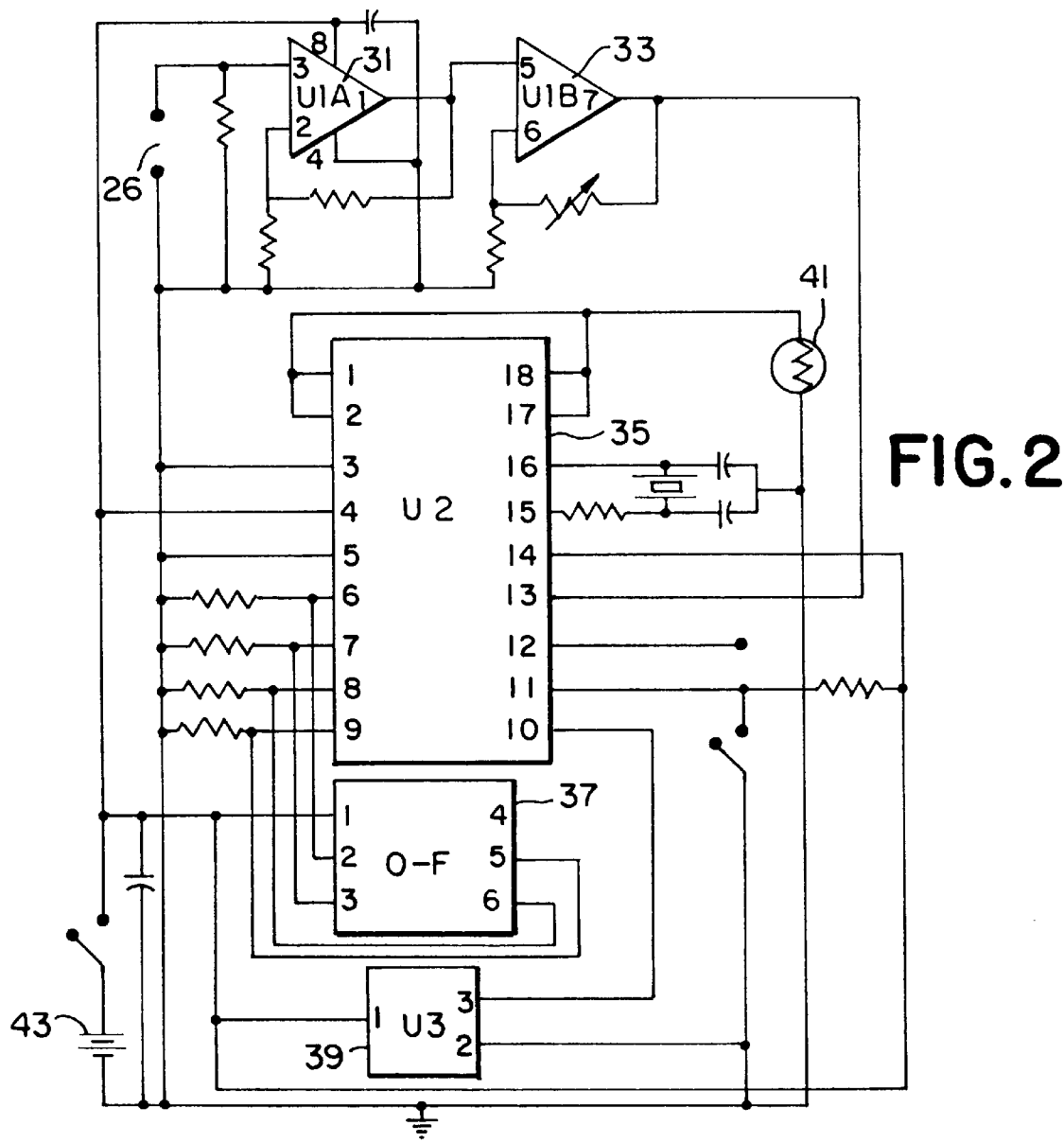
FIG. 2 is a circuit diagram of the present invention illustrating the preferred embodiment as it is designed for use with an epileptic child needing daytime motion supervision.

FIG. 2 shows the motion detection monitor that can employ the sensor of this invention. It is to be understood, however, that other sensors that provide similar data are also usable with the present monitor. All that is required is that an electronic signal responsive to movement of the sensor be generated by the sensor in response to a first condition representing a medical condition and the second condition representing casual motion.

Shown in FIG. 2 is a schematic view of the monitor electronics for the preferred embodiment of the present invention. The monitor shown is for daytime activity. It can be used for nighttime monitoring; however, the type of alarm and the power supply used may to be altered for nightime conditions.

The alarm 41 for the daytime monitor shown in FIG. 2 is an acoustic transducer. The audible signal is different for a potential medical disorder than for a low battery warning. If a potential medical event is detected, switch 37 settings determine whether the alarm is active until the monitor is manually reset, or, alternatively, if it automatically resets after a preselected time.

In the embodiment shown in FIG. 2, the sensor output from wires 25 is amplified by a pair of low-power operational amplifiers 31 and 33 that present a fixed input impedance to the sensor of FIG. 1. This signal is analyzed by micro controller 35 to determine if the activity in the sensor resembles a medical disorder or casual motion. Sensor activity/or lack of activity within sequences of preselected time intervals is used to discriminate a potential medical disorder from casual motion. A hex rotary switch 37 sets the time interval and total sampling time used by processor 35. The gain for amplifier 33 is also adjustable. This combination of user detectable parameters permit an unlimited range of settings to accommodate a wide variety of disorders. If processor 35 detects an event indicative of a medical problem, or alternatively if battery monitor 39 signals a low-battery condition, an alarm from alarm 41 is given. The listing for a preferred micro processor 35 used in the embodiment described herein (Microchip PIC16LC71) is shown below in Table I.

Power for the daytime monitor shown in FIG. 2 is derived from a standard 3 VDC coin cell battery 49. The estimated battery life using a Panasonic CR2032 battery is four school years, assuming the monitor is used for six hours/day, nice months/year.

An alternative monitor for nighttime activity can be used as well, being selected by the user at time of going to bed. A switch and an FCC compliant radio frequency signal generator may replace alarm 41 and send a signal to a remote, compatible receiver when the alarm criteria are satisfied. The receiver then activates the desired alarm mechanism, whether remote or on site. The signal is retransmitted periodically until the monitor is manually reset. In addition to a remote alarm, an LED on the monitor may be provided to continuously flash at a rate that indicates if the alarm is a result of a potential medical even or a low battery.

Power for the nighttime monitor can be derived from a standard miniature 12 volt battery. A low-dropout precision voltage reference is utilized to supply 4 volts to the monitor circuitry. The estimated life of a standard alkaline battery is six weeks.

In operation, gain and timing parameters are adjusted to match the patient, taking into consideration size, weight, medical problems and anticipated activity, for example. The monitor is powered on and attached to the patient at a location on the patient where the medical disorder is manifested as anomalous physical activity. In an effort to conserve battery life, no indicator is present to notify the user when it is operational. Instead, the monitor beeps twice (in the daytime mode shown in FIG. 2) or the LED flashes twice (in the nighttime mode) when it is first turned on. This notifies the user that the battery voltage is adequate and unit is operating properly. If this does not occur, the battery needs replacement. If it still does not occur when a new battery is installed, the unit is malfunctioning and should not be used.

Presented below is Table I, showing the code listing for the above described micro processor.

TABLE I

Code Listing
(daytime monitor)

```
; micro code for the daytime event monitor
;   RA0 = alarm output (digital)
;   RA1 = alarm output (digital)
;   RA2 = alarm output (digital)
;   RA3 = alarm output (digital)
;   RA4 = N/C input (digital)
;   RB1, RB0, RB3, RB2 = config input:
;   hex    1234    w(ms)    time(s)    count    timer enable
;   0      0000    1000     5          5        1
;   1      0001    1000     10         10       1
;   2      0010    750      5          7        1
;   3      0011    750      10         13       1
;   4      0100    500      5          10       1
;   5      0101    500      10         20       1
;   6      0110    250      5          20       1
;   7      0111    250      10         40       1
;   8      1000    1000     5          5        0
;   9      1001    1000     10         10       0
;   A      1010    750      5          7        0
;   B      1011    750      10         13       0
;   C      1100    500      5          10       0
;   D      1101    500      10         20       0
;   E      1110    250      5          10       0
;   F      1111    250      10         40       0
;   RB4 = battery interrupt
;   RB5 = debug in (high -> normal operation, low -> debug mode)
;   RB6 = debug out
;   RB7 = sensor input (hight = 0.36 Vdd)
;   Vss = ground = Vpp;
;   Vdd = 3.0 Vdc
RTCC      equ     01h
PC        equ     02h
STAT      equ     03h
FILEREG   equ     04h
PORTA     equ     05h
PORTB     equ     06h
ADCON0    equ     08h
ADCON1    equ     88h
ADRES     equ     09h
PCLATH    equ     0Ah
INTCON    equ     0Bh
TRISA     equ     85h
TRISB     equ     86h
DELAY 1   equ     0ch
DLY1      equ     0dh
DLY2      equ     0eh
_nms_1    equ     0fh
_nms_2    equ     10h
```

TABLE I-continued

Code Listing
(daytime monitor)

```
__nms__3    equ     11h
WIN1        equ     12h
WIN2        equ     13h
DBG         equ     14h
COUNTx      equ     15h
BEEP1       equ     16h
BEEP2       equ     17h
EVENT       equ     18h         ;event flag
COUNT       equ     19h
ALARM       equ     1ah         ;0->seizure, 1-.battery
START_UP    equ     1bh
CFG         equ     1ch
BEEP_ON     equ     1dh
BEEP_OFF    equ     1eh
RTCC_C      equ     1fh
TEMP        equ     20h
GFG_IN      equ     21h
OSC         equ     b'00001111'
MASK        equ     b'00001111'
            org     h'0000'
     bsf    START_UP,0  ;location 0000
            goto    start       ; location 0001
            goto    start       ; location 0002
            goto    start       ; location 0003
;    interrupts occur at location 4
;    DON'T use instructions that affect STATUS or W !!!!
            btfsc   INTCON,2    ; RTCC timer interrupt?
            goto    int_b
            btfsc   INTCON,0    ;clear RB port change interrupt
            btfsc   INTCON,3    ;clear mismatch condition
            btfsc   INTCON,0    ;just in case
            btfss   PORTB,4     ;battery low?
            goto    int_a
            bsf     EVENT,0     ;sensor change
            return              ;don't set GIE bit! let __nms finish!
int_a       bsf     ALARM,0     ;battery low
            goto    alarm
int_b       bcf     INTCON,2    ;clear RTCC interrupt
            secfsc  RTCC_C      ;RTCC count
            retfie
start       clrf    INTCON      ;initially disable interrupts
            movlw   b'00000011' ;RA0,RA1,RA2,RA3=digital
            movlf   ADCON1
            movlw   b'00010000' ;define PORTA inputs &
                                outputs,AFTER ADCON!
            tris    PORTA
            clrf    PORTA
            movlw   b'10111111' ;port B is all inputs, except RB6
            tris    PORTB
            clrf    PORTB
            clrf    ALARM
            movlw   7           ;approx 60 seconds of alarm
            movwf   RTCC_C
            call    __400ms
            call    __400ms
            call    __400ms
            call    __400ms
battery     btfss   PORTB,4     ;wait for MAX809 to set,
                                if no set-no beeps
            goto    battery     ;problem if battery dies (RB4->0),
                                see above
            btfsc   START_UP    ;just powered up?
            call    beep__2
            clrf    START_UP
            call    config      ;read config settings & store values
            incf    COUNT       ;for the loop (DECFSZ)
            btfss   PORTB,5
            call    debut       ;YES, debug changes DLY1 &
                                DLY2, but so what!
            movlw   b'10001000' ;enable RB port change only
            movlw   INTCON
            sleep               ;sleep until battery dead or
                                sensor change
            movlw   COUNT
            movlw   COUNTx
acquire     desfsz  COUNTx      ;willgo here upon wake-up
            goto    loop
            goto    alarm
loop        clrf    EVENT
            bsf     INTCON,3    ;RB port disabled in interrupt
                                service routine
            bsf     INTCON,7    ; GIE bit resent in interrupt
                                service routine
            call    __WINms     ;delay window width; !!! MAKE
                                SURE NO OTHER __nms CALLS !!!
            bsfsc   EVENT,0     ;port change during delay?
            goto    acquire     ;port change occurred during delay
            goto    start
alarm       clrf    INTCOM      ;forces manual reset alarm mode
            btfsc   ALARM,0
            goto    alarm2
            clrwdt
            movlw   b'10000111'
            option
            clrf    RTCC
            movlw   b'10100000' ;enable RTCC only if timer enabled
                                on RB3
            btfss   PORTB,2     ;bit 2 = 1 disables auto-shut
                                down mode
            movfw   INTCON
alarm1      call    beep__1     ;possible seizure
            goto    alarm1
alarm2      call    beep__2     ;battery
            goto    alarm2
config      movwf   CGF
            cirf    CFG_IN      ;swap bits 2&3 and 0&1 because of
                                circuit
            btfsc   PORT,3
            bsf     CFG_IN,2
            btfsc   PORTB,2
            bsf     CFG_IN,3
            btfsc   PORTB,1
            bsf     CFG_IN,0
            btfsc   PORTB,0
            bsf     CFG_IN,1
            movfw   CFG_IN
            andlw   b'00001111'
            addwf   PC          ;offset PC by the amount in w
                                (cute huh?)
            goto    zzero       ;the defaults
            goto    one
            goto    two
            goto    three
            goto    four
            goto    five
            goto    six
            goto    seven
            goto    zzero
            goto    one
            goto    two
            goto    three
            goto    four
            goto    five
            goto    six
seven       movlw   40
            movwf   COUNT
            movlw   2
            movwf   WIN2
            movlw   170
            movwf   WIN1
            return
six         movlw   20
            movwf   COUNT
            movlw   2
            movwf   WIN2
            movlw   170
            movwf   WIN1
            return
five        movlw   20
            movwf   COUNT
            movlw   3
            movwf   WIN2
```

TABLE I-continued

Code Listing
(daytime monitor)

```
              movlw   288
              movwf   WIN1
              return
four          movlw   10
              movwf   COUNT
              movlw   3
              movwf   WIN2
              movlw   288
              movwf   WIN1
              return
three         movlw   13
              movwf   COUNT
              movlw   4
              movwf   WIN2
              movlw   255
              movwf   WIN1
              return
two           movlw   7
              movwf   COUNT
              movlw   4
              movwf   WIN2
              movlw   255
              movwf   WIN1
              return
one           movlw   10
              movwf   COUNT
              movlw   5
              movwf   WIN2
              movlw   255
              movwf   WIN1
              return
zzero         movlw   5           ;5 - 1 second windows
              movwf   COUNT
              movlw   5
              movwf   WIN2
              movlw   255
              movwf   WIN1
              return
beep_1        movwf   BEEP1
              call    beep_off
              call    _400ms
              call    beep_40
              call    beep_off
              call    _400ms
              movfw   BEEP1
              return
beep_2        movwf   BEEP2
              call    beep_off
              call    _400ms
              call    beep_40
              call    beep_off
              call    _40ms
              call    _40ms
              call    _40ms
              call    _40ms
              call    beep_40
              call    beep_off
              call    _400ms
              movfw   BEEP2
              return
beep_off      movwf   BEEP_OFF
              clrf    PORTA
              movfw   BEEP_OFF
              return
debut         movwf   DBG         ;output configuration settings
              movfw   COUNT
              movwf   COUNTx
              bcf     PORTB,6
              call    _400ms      :first zero volts for 400ms
              bsf     PORTB,6
              call    _40ms       ;show 40ms puslе
              bcf     PORTB,6
              call    _400ms      ;wait another 400ms
              bsf     PORTB,6
              call    _WINms      ;show window width
              bcf     PORTB,6
```

TABLE I-continued

Code Listing
(daytime monitor)

```
              call    _400ms      :wait another 400ms
              bsf     PORTB,6
debug_a       desfxz  COUNTx      ;show entire time (window*count)
              goto    debug_b
              goto    debut_c
debug_b       call    _WINms
              goto    debug_a
debug_c       bcf     PORTB,6
              call    _400ms
debug_d       movfw   PORTG       ;just keep showing sensor input
              movwf   DBG         ;you can't just rrf w register
              rff     DBGw
              andlw   b'01000000'
              movwf   PORTB
              goto    debug_d
              movfw   DBG
              return
_nms          movwf   _nms3
              clrf    _nms_2
_nmsa         movfw   _nms_2
              xorwf   DLY2,w
              btfss   STAT,2      ;need at least 1 in DLY_2
              goto    _nmsb
              movfw   _nms_3      ;done, restore w
              return
_nmsb         incf    _nms_2
              clrf    _nms_1
_nmsc         incf    _nms_1
              movfw   _nms_1
              sorwf   DLY1,w
              btfss   STAT,2
              goto    _nmsc
              goto    _nmsa
```

While particular embodiments of the present invention have been illustrated and described herein, it is not intended that these illustrations and descriptions limit the invention. Changes and modifications may be made herein without departing from the scope and spirit of the following claims.

We claim:

1. A motion detecting device monitoring daytime patient movement, comprising:

a sensor adapted to generate a voltage from mechanical vibrations, comprising: a housing having an outer shell and a hollow spherical opening therein; a plurality of inner spherical bodies adapted to move freely inside spherical opening to produce detectable mechanical vibration in said other shell; a piezoelectric film attached to a portion of said outer shell, said film being adapted to generate said voltage from said mechanical vibrations, and circuit means in operable relationship with said voltage for generating an alarm upon detection of a predetermined signal, said circuit including impedance means presenting a fixed impedance to said sensor; a micro controller means for analyzing said signal to select from a first and second condition by sensing activity within sequences of preselected time intervals, said first condition representing a medical condition and second condition representing casual motion; switch means for setting a time interval and a total sampling time for said micro controller; and alarm signal generating means for generating an alarm upon detection by said microprocessor of a predetermined activity.

2. The motion detection device of claim 1, wherein said outer shell comprises a pair of cylinders having a hemispherical volume removed therefrom to form said spherical opening.

3. The motion detection device of claim 2, wherein one of said cylinders includes a smooth surface for attachment of said piezoelectric film.

4. The motion detection device of claim 2, wherein one of said cylinders includes a smooth surface for attachment of said piezoelectric film.

5. The motion detection device of claim 1, which further includes nighttime detection means including a switch to selectively activate a radio transmitter to transmit said alarm signal and a remote compatible receiver for receiving said transmitted signal to activate an alarm means.

6. The motion detection device of claim 5, which further includes a reset means for resetting said device to an operable condition after activation of said alarm.

7. The motion detection device of claim 1, which further includes a reset means for resetting said device to an operable condition after activation of said alarm.

* * * * *